United States Patent

Plant Pat. 3,932

Patented July 6, 1976

3,932

ORCHID NAMED MOLIERE (VALECOR)

Maurice Lecoufle and Michel Vacherot, Boissy-St.-Leger, France, assignors to Les Petits-fils et fils de Vacherot and Lecoufle, Boissy-Saint-Leger, France Filed Mar. 24, 1975, Ser. No. 561,324

Int. Cl.[2] A01H 5/00

U.S. Cl. Plt.—68 1 Claim

ABSTRACT OF THE DISCLOSURE

A new variety of orchid plant of the genus Odontonia distinguished by its vigorous growth habit and rapid production of new bulbs which produces floriferous plants of large size having many long arching stems of excellent appearance which permits a very good planting density. The flowers are spaced regularly in alternate order on a long petiole and are well separated from each other, each being of large size with excellent texture and durability and with attractive commercially favorable colors. The plant blooms naturally over a long part of the year with its peak of production in the spring and it can be forced to produce whenever a growth is achieved.

*Background of the New Plant*

Our new variety of orchid plant was selected from a group of seedlings resulting from a crossing of Odontonia Astrolabe (unpatented) and Odontoglossum Nabella (unpatented) made by us in Boissy-Saint-Leger, France, with the objective of developing a hybrid which would flower abundantly over a very long period of the year and with full production in the spring.

This plant was selected for test and culture because of its vigorous growth habit and rapid production of new bulbs, its apparent fulfillment of our objectives, and its very attractive coloration. Asexual reproduction of our new plant was done by us at Boissy-Saint-Leger, France, by meristematic tissue culture and successive generations of mericlones of this plant have demonstrated that all of its distinctive and advantageous characteristics hold true from generation to generation and appear to be firmly fixed.

For the generic identification of our new orchid plant, we have adopted the name Moliere and for its commercial exploitation, this cultivar is to be known as Valecor.

*Description of the Drawings*

This new variety of orchid plant is illustrated by the accompanying drawings, in which.

Figure 1:
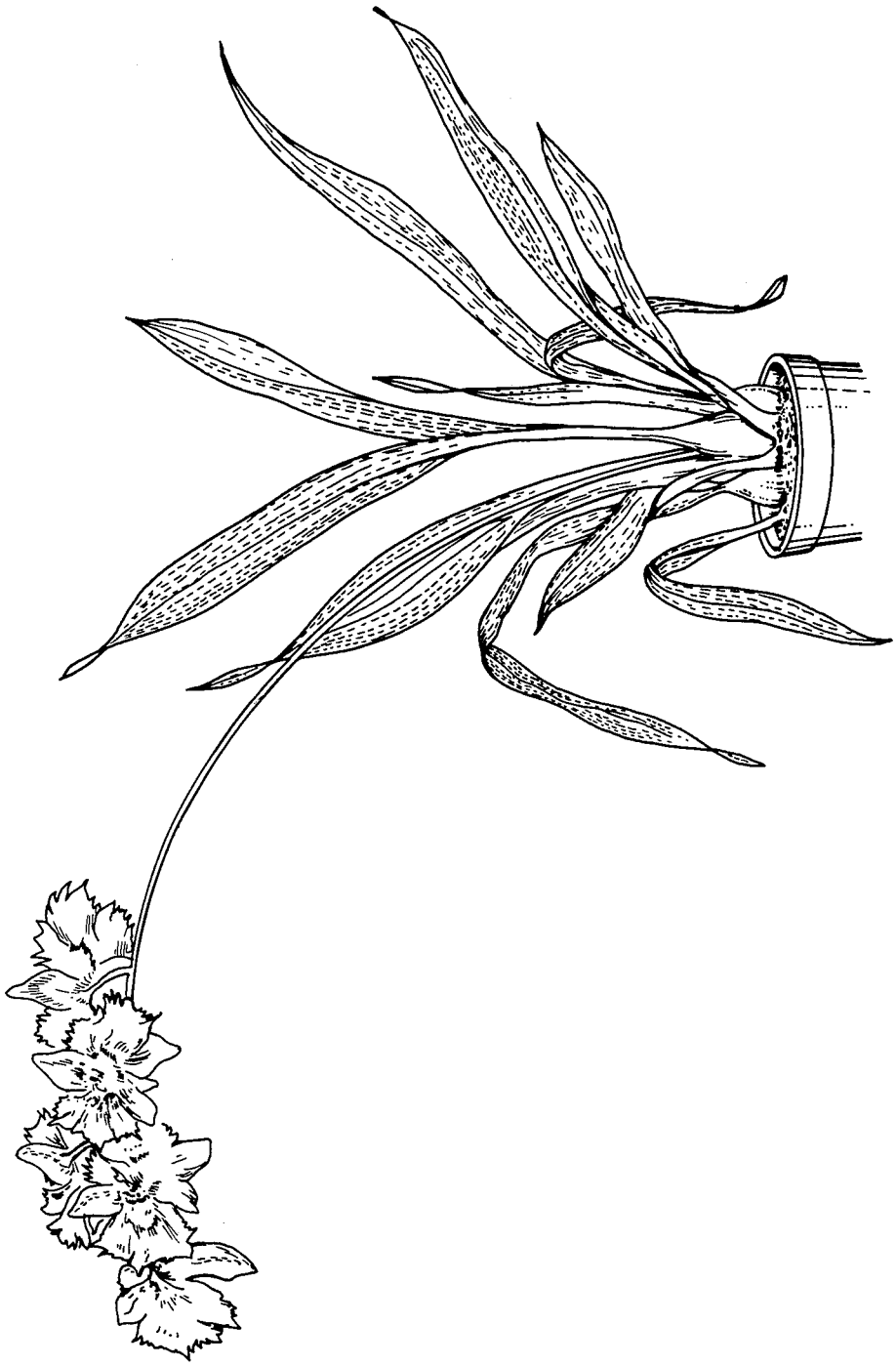
FIG. 1 is a sketch which shows a typical adult plant.
Figure 2:
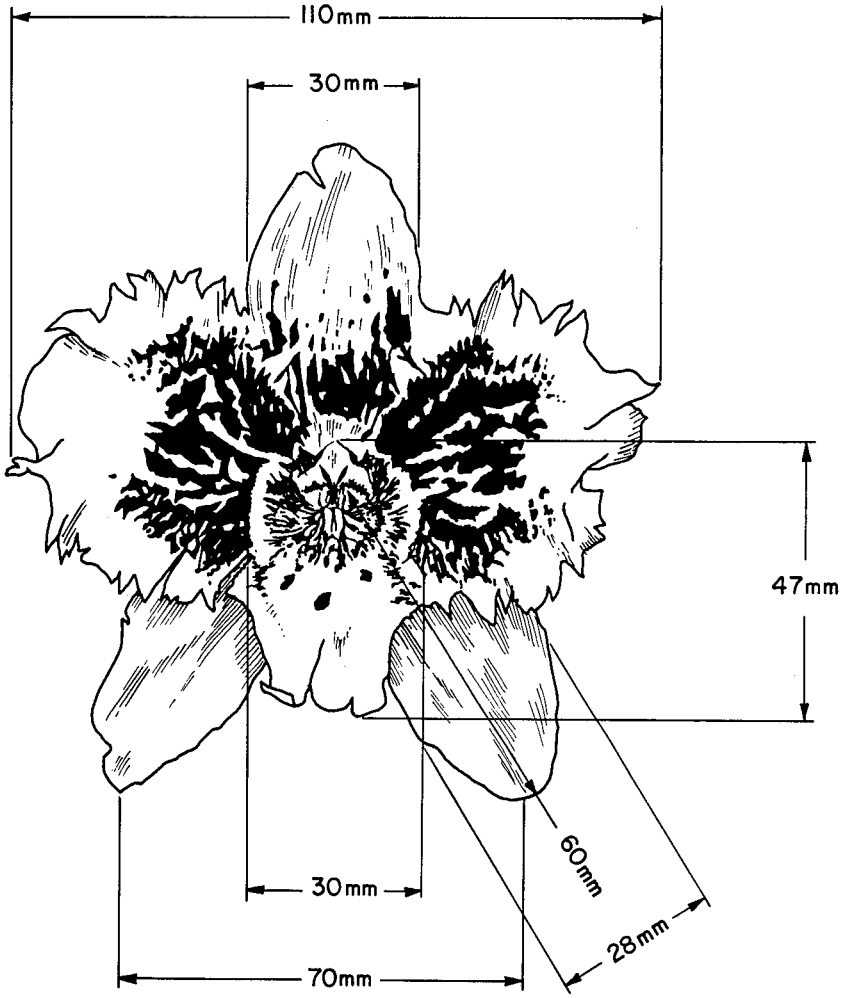
FIG. 2 is a sketch showing a stem of the plant with open flowers.
Figure 3:
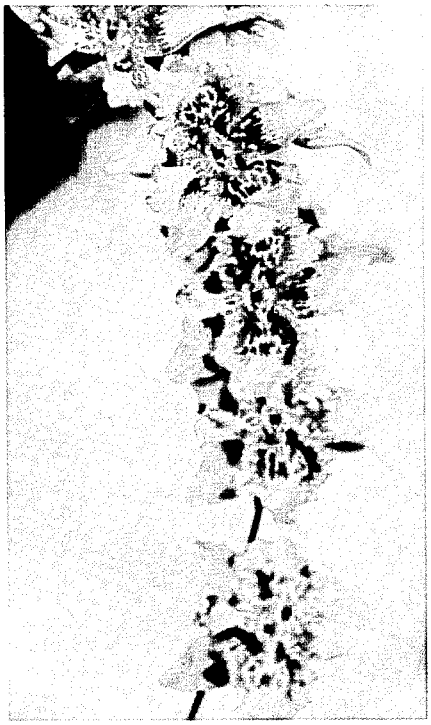
FIGS. 3 and 4 are photographic views in full color showing a typical flowering stem of this cultivar and a close-up face view of one of the flowers, the color reproduction being as accurate as is reasonably possible to obtain by commercial photographic procedures.
Figure 4:
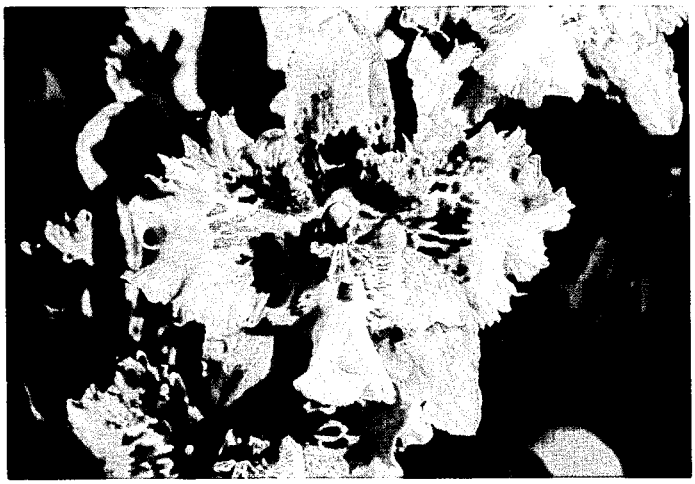

*Description of the New Variety of Orchid Plant*

The following is a detailed description of our new variety of orchid plant with color designations according to the R.H.S. Colour Chart published by The Royal Horticultural Society at London, England.

THE PLANT

When young, the plant is not particularly distinguishable from several other Odontonia plants of the same GREX. When the plant is adult, however, it has special characteristics which distinguish it from all others.

Origin: Seedling.

Parentage:
- Male Parent—Odontoglossum Nabella (unpatented).
- Female Parent—Odontonia Astrolabe (unpatented).

Classification:
- Botanic—Odontonia hybrid.
- Commercial—Odontonia mericlone.

Form: Herbaceous.

Height:
- Flower Stem—50 to 100 cm. from the base.
- Leaves—30 to 50 cm. from the base.

Bulb: The front bulb is of oblong form somewhat like that of an upright pear ending in an apex with two long leaves. It has at its base three pairs of leaves enveloping the bulb from opposite sides, but only two of these leaves develop into long leaves like those growing from the apex; all the other leaves remain dwarf. The bulb can bear two spikes, one on each side of the bulb, but many times only one spike will flower. When exceptionally well grown, the bulb will also flower from its apex with one or more spikes.
- Size: The front bulb of the adult plant is about 5.5 cm. wide and 9 to 10 cm. high, these being only average sizes.
- Number: When adult, a plant has at least three well formed bulbs with leaves. The number of bulbs may increase each year thereafter.

Leaves:
- Size:
  - Length—From 30 to 50 cm.
  - Width—6 cm. at largest part.
- Shape: Lanceolate with acuminate apex, folded on a central rib at the base and being almost flat toward the tip.
- Venation: Base to Tip Color—Dark Green.

Petioles: The base of each lateral leaf forms a petiole attached to the bulb, the petiole being about 6 to 8 cm. long and 2 to 2.5 cm. wide, and having practically the same color as the leaf.

Stems: The flowering stem is usually from 50 to 100 cm. in length, the first flower appearing about about 30 to 80 cm. from the base of the stem. The entire length of the stem has nodes spaced about 4 to 8 cm. apart and each of these nodes is sheathed with amplexicaul bracts.

THE FLOWER

Blooming Habit: Recurrent. The plant flowers regularly over a long period of the year with normal full bloom in the spring, but this plant produces its flowers whenever its growth is achieved.

Borne: In simple racemose manner, the distance between the flowers, which are alternate, being about 3 cm. The blooms appear on an arching spray with the flowers attached on each side of the stem. An adult plant produces about 10 to 12 flowers on each stem, but this may vary from 1 to 20 according to the size and age of the plant. The second stem, however, has less flowers.

Average Size: Large. The corolla is formed by 3 sepals, 2 petals, and a labellum. The flower measures 70 mm. between the tips of the 2 lateral sepals and about 110 mm. between the tips of the 2 petals.
- Sepals:
  - Length—About 60 mm. Width (Average)—Lateral sepals: 28 mm. Dorsal sepal: 30 mm.
- Petals:
  - Length—50 mm. with wide undulating and irregularly incised margins.
  - Width—55 mm.
- Labellum: Width of about 30 mm. and length of about 47 mm. The height is 45 mm.
- Gynostemium: Length—About 15 mm.

Shape of petals and Sepals: The petals are much wider than the sepals but have an acute tip. They are fringed and denticulated at the edges.

Color:

Sepals: Overall White with a light wash of Purple varying from RHS 75A to 75C extending over the outer two-thirds of the central area leaving wide White margins, the base of the sepals having a large central blotch of RHS 184A and spots of 182A spreading laterally to the margins.

Petals: Overall White with a central one-half to two-thirds of the petal area spotted with irregular blotches of RHS 183A, the lateral blotches fading to 182B as they spread toward the petal margins, the petals having wide White margins from end-to-end.

Labellum: Amber Yellow of the Yellow-Orange Group 18A in the center and freckled around the margin with Golden Brown red spots of the Greyed Orange Group 164A and fading to 164C. There are also other little spots of ordinary Maroon of the Greyed Orange Group 166B, all of these colors on a White background.

Peduncle: Each flower is carried by a peduncle of 40 to 44 mm. long forming an almost acute angle with the stem. At each flower peduncle, there is a very small amplexicaul bract embryo.

It will be understood that the dimensions and the colors of this new plant may vary somewhat under various conditions of growth and quantity of light given during blooming periods. When plants of this variety bloom in the spring, with much light, the colors are more brilliant. When the temperature is not controlled, however, it is recommended that this variety not be allowed to flower.

We claim:

1. The new and distinct variety of orchid plant of the Odontonia species substantially as herein shown and described, characterized by its vigorous growth habit and rapid production of new bulbs, its abundant production of large, well-formed flowers, the attractive coloring of the flowers, and its relatively long blooming period.

No references cited.

ROBERT E. BAGWILL, Primary Examiner